United States Patent [19]

Richter et al.

[11] 4,418,422
[45] Nov. 29, 1983

[54] AIMING DEVICE FOR SETTING NAILS IN BONES

[75] Inventors: Karl M. Richter, Wentorf; Hans E. Harder, Probsteirerhagen; Klaus Behrens, Rickling, all of Fed. Rep. of Germany

[73] Assignee: Howmedica International, Inc., Schonkirchen, Fed. Rep. of Germany

[21] Appl. No.: 242,679

[22] Filed: Mar. 11, 1981

Related U.S. Application Data

[63] Continuation-in-part of Ser. No. 7,308, Jan. 29, 1979, abandoned.

[30] Foreign Application Priority Data

Feb. 22, 1978 [DE] Fed. Rep. of Germany ....... 7805301

[51] Int. Cl.³ .............................................. G21K 5/08
[52] U.S. Cl. ............................... 378/205; 128/92 EB; 378/162
[58] Field of Search ....................... 378/163, 205, 162; 128/92 BA, 92 BB, 92 EB

[56] References Cited

U.S. PATENT DOCUMENTS

| 3,178,574 | 4/1965 | Stryker | 378/163 |
| 3,577,160 | 5/1971 | White | 378/163 |
| 3,704,707 | 12/1972 | Halloran | 378/162 |
| 4,005,527 | 1/1977 | Wilson et al. | 378/163 |
| 4,088,893 | 5/1978 | Schroeder | 378/205 |

Primary Examiner—Alfred E. Smith
Assistant Examiner—T. N. Grigsby
Attorney, Agent, or Firm—Andrus, Sceales, Starke & Sawall

[57] ABSTRACT

A device for positioning a holder for an aiming sleeve for implanted bone nail fasteners with respect to a Roentgen ray source includes a support (25) for supporting the holder (7). A base plate (12) and a pivotable bracket plate (3) receives the support means and is mountable on the housing of the Roentgen ray source for spacedly positioning the holder from the source. The support is formed as a fork-like element (26, 28, 29) retained in sleeves (38, 39) on the bracket plate by means of locking cams (8).

10 Claims, 5 Drawing Figures

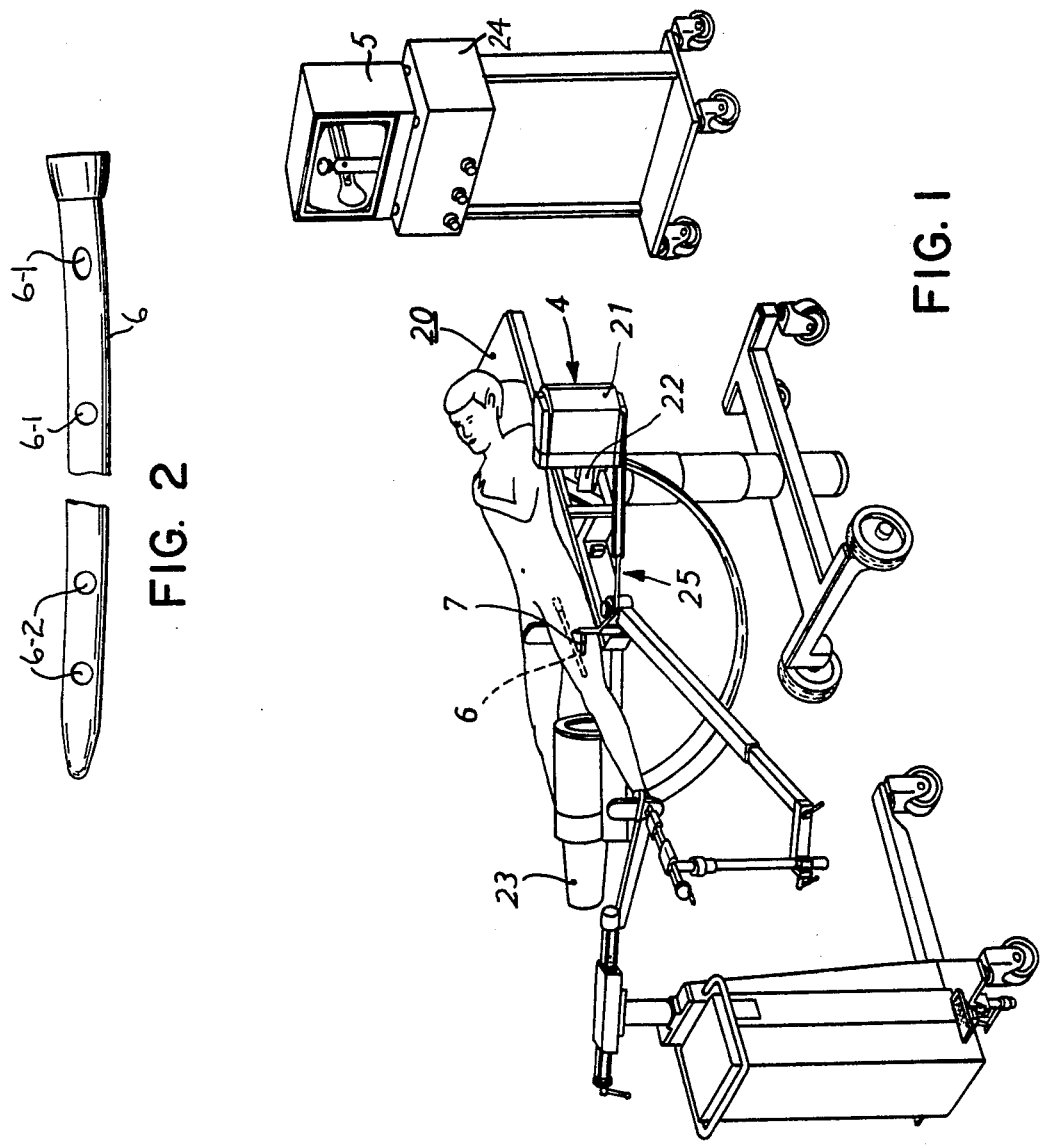
FIG. 2
FIG. 1
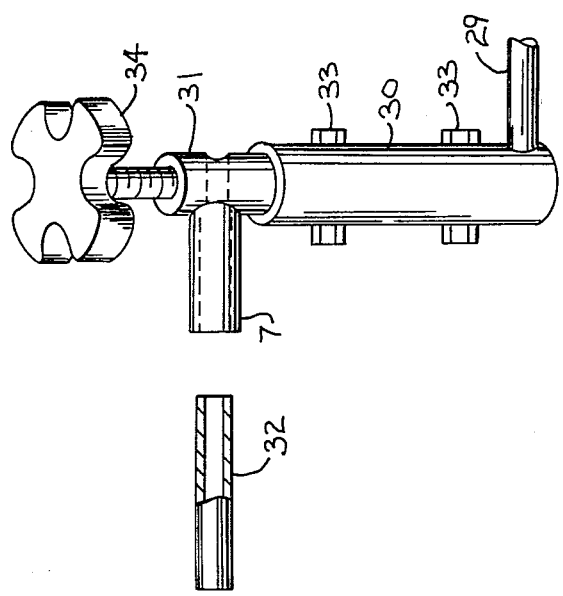
FIG. 4

AIMING DEVICE FOR SETTING NAILS IN BONES

CROSS REFERENCE TO RELATED APPLICATION

The present application is a continuation-in-part application of U.S. patent application Ser. No. 007,308, filed Jan. 29, 1979 and now abandoned.

TECHNICAL FIELD

The invention refers to a distal aiming device for the nail setting of bones.

BACKGROUND ART

In a common orthopedic technique for repairing broken or shattered bones, an elongated metal pin or nail is inserted along the central portion of the bone. The nail strengthens the bone and holds the parts of the bone together. Such a technique is often used in repairing the femur, the bone that connects the pelvis with the knee, or the tibia, one of the bones that connects the knee with the ankle. To insure that the parts of the bones are maintained together and in the correct position, transverse fasteners extend through the bone and the pin at each end. The pin contains holes at each end for this purpose.

In the surgical procedure, the bone is reamed out and the pin inserted along the central portion. However, once the pin is lodged in the bone, a problem arises. How does the surgeon know where to drill the fastener holes in the bone so that they will line up with the preestablished holes in the pin, thus permitting insertion of the fasteners?

For the proximal end of the pin, that is, the end nearest the point of insertion, a jig may be fastened to the exposed end of the pin. The jig extends along the bone and positions aiming sleeves that provide the necessary guide to the drill.

However, the problem is more difficult for the distal end of the pin, that is, the end buried in the bone. Jigs connected with the pin have been used to aim at the distal perforations or bores in the locking pin. However, due to the curved shape of bones, such as the femur, and the danger that the pin might twist during setting of the pin, the known device is not well suited.

DISCLOSURE OF THE INVENTION

The fundamental object of the invention is thus to provide an aiming device for pin or nail setting at the distal end of the pin wherein the aiming procedure can be made in a rapid manner, surely, and without complications.

This problem is solved such that socket means for the aiming sleeve is attached to a housing for an X-ray source and positioned at a distance from the exit window of the ray source and substantially coaxial to the main beam path of the ray source.

The aiming procedure using the invention starts with placing the X-ray source, i.e. its beam path, perpendicularly to the longitudinal axis of the pin or nail and centering it with respect to a distal hole or bore of the pin or nail. The X-ray image occuring in receiver means is for example transmitted from the receiver means to a monitor through a multiplier, whereupon the hole of the pin or nail inclusive other parts can be seen on the monitor screen. By changing the position of the aiming device and/or the position of the patient, the image of the hole can be brought into an overlapping position with the socket of the aiming sleeve, so that the axis of the aiming sleeve is coaxial with the axis of the hole.

After making an incision, the aiming sleeve for the femur or the tibia, is inserted in the socket and moved up to the corticalis and fixed in this position. All the other steps, such as incision, making bores, tightening of the screws and so on can be made by means of the aiming sleeve.

It is, in addition, possible to make a check after each operative phase and if necessary to again adjust the aiming device.

For mechanical reasons and in order to achieve a simple and suitable adjustment, it is preferred to use a receiving bushing or socket in which the aiming sleeve is slidably received and which can be fixed in selected positions.

The socket for the aiming sleeve is fixed to the housing of the X-ray source through an appropriate retaining means, so that it may be placed at a distance from the exit window of the source within the main beam path. A particular embodiment of the invention provides for this reason that the socket for the aiming sleeve is slidably mounted with respect to the housing. The sliding support of the sleeve enables the operator to adjust the desired distance with respect to the leg of the patient.

The retaining means for the socket of the aiming sleeve can be designed in any suitable way. An additional embodiment of the invention provides in this respect fo the aiming sleeve socket to be mounted on bifurcated support means and two bushes fixed to the housing to accommodate the fork ends of prongs. By means of the bifurcated support the aiming sleeve socket can be continuously adjusted.

In order to maintain the adjusted position of the socket, another embodiment of the invention provides that the housing of the X-ray source arranged thereat has at least one arresting adjusting element that fixes the fork in a selected position.

In order to fix the fork on the housing another embodiment of the invention provides on the housing of the X-ray source a bracket carrying the bushes for the fork prongs.

In order to have as little obstruction as possible, the fork is fixed on the bottom side of the housing. To facilitate the insertion of the fork, which is preferably made of sterilizeable material, an additional embodiment of the invention provides that the bracket be composed of a base plate connected rigidly to the housing and a bracket plate retaining the bushes and pivotally supported at the base plate. For the insertion of the fork the pivotable bracket plate is pivoted downwards and thereafter pivoted back again to its starting position. So that the plate remains in its working position, another embodiment of the invention provides that on the base plate there is a hand operated locking mechanism and the pivotable bracket plate includes a locking portion that can be brought into interlocking engagement with the locking device. The locking means is suitably designed such that the interlocking portion becomes automatically arrested when the plate is pivoted back into its working position. Other advantageous embodiments of the invention are described below.

BRIEF DESCRIPTION OF THE DRAWINGS

A preferred embodiment of the invention is described in more detail by way of the attached drawings.

FIG. 1 shows in a perspective view an example for the use of the aiming device according to the invention.

FIG. 2 shows a pin or nail suitable for use in the femur.

FIG. 4 shows a portion of the aiming gauge according to FIG. 3.

BEST MODE FOR CARRYING OUT THE INVENTION

Figure 5:
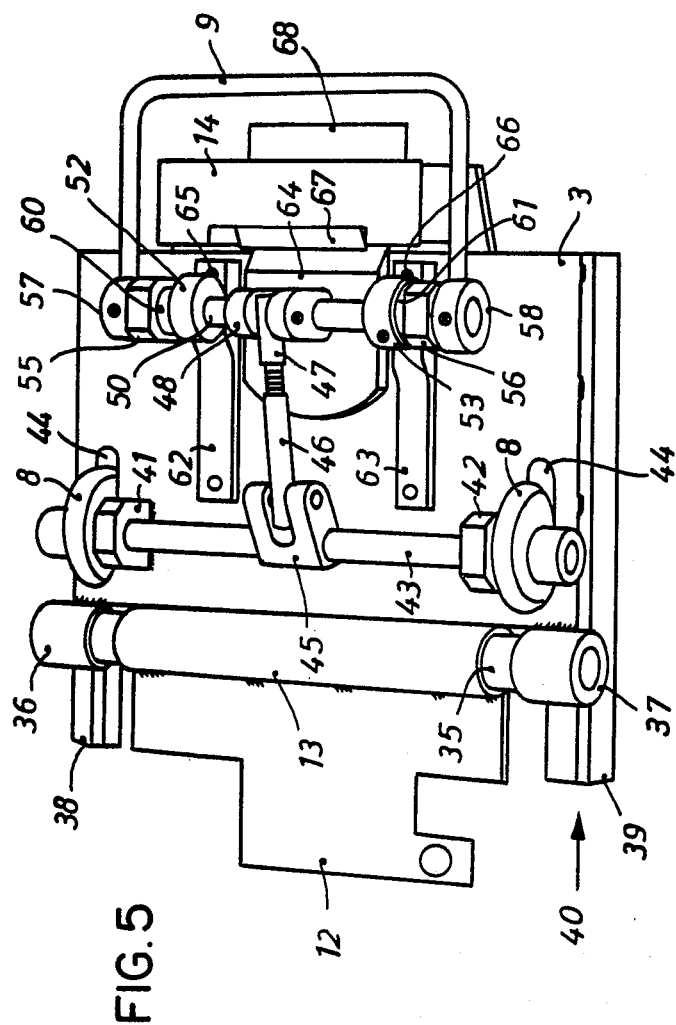
FIG. 5 shows a perspective view of a support device for the aiming gauge as illustrated in FIGS. 3 and 4.

Before passing more specifically to the details represented in the drawings, it should be noted that each described part is of essential importance for the invention, either in combination with the features of the claims or simply in itself.

On an operating bed 20 there is resting a patient, in whose left femur there is implanted a locking nail 6 (indicated with dotted lines). A source 4 for X-rays is placed in a movable position with respect to the operating bed 20 and has a housing 21, including at the front an exit window 22. A receiver 23 is located in the beam path of the Röntgen generator 4, the receiver being operatively connected to a monitor 5 which is controlled through an image amplifier 24.

Nail 6 is shown in FIG. 2 to include fastener holes 6-1 in the proximal end thereof and fastener holes 6-2 in the distal end thereof.

Below the housing 21 of the generator is fixed an aiming gauge indicated generally with 25, which at its forward end has a reception socket 7 which is placed centrally with respect to the main beam path of the radiation socket 4.

Figure 3:
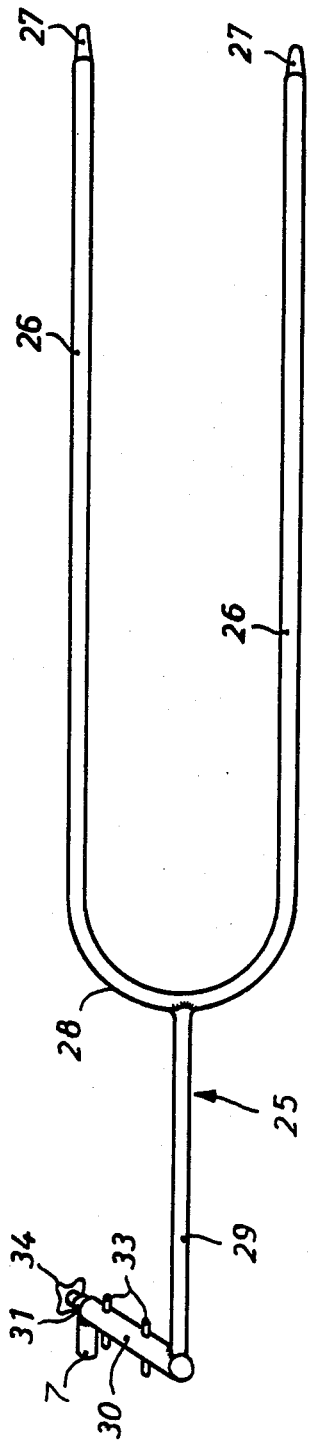
FIG. 3 shows an aiming gauge for the aiming device according to FIG. 1.

The aiming gauge 25 is illustrated in FIG. 3 in larger scale. It comprises a fork having two prongs 26 which are circularly formed in cross section. Plastic plugs 27 are inserted in the free extremities of the prongs 26, which at their projecting extremities are configured as points. The prongs 26 of the fork 25 are made by bending from an single elongated rod and thus are connected with each other through a circular portion 28. The center of the circular portion 28 is connected to a leg 29, preferably by welding. At the free end of the leg 29 a transverse portion 30 is welded thereto, extending in a plane perpendicular with respect to the plane defined by the prongs 26. The transverse portion 30 has a tubular shape and telescopically accommodates at the end thereof a tube 31 which in turn is crossed by reception socket 7. The retaining tube 31 is fixed inside the tube 30 with the aid of screws 33 and can be fixed at gradual distances in the tube 30. Reception socket 7 has a throughgoing staggered bore with the narrower part extending across the retaining tube 31. The reception socket serves to receive an aiming sleeve 32, that can be fixed in the socket 7 with the aid of a star shaped knob 34.

FIG. 5 shows a support system for the aiming gauge 25 according to FIG. 3. It comprises a base plate 12 that is fixed on the underside of the housing 21 of the generator (FIG. 1) for example with the aid of screws. Pivotally connected to the base plate 12 through a hinge is a bracket plate 3. The hinge comprises a bushing bearing 13 welded to the base plate 12 and having a support rod 35 extending therethrough which in turn is mounted to be capable of rotation in two pivot bearings 36 and 37. The pivot bearings 36 and 37 are welded on the pivotable bracket plate 3. Sleeves 38 and 39 are welded on both sides of bracket plate 3 dimensions such and placed at such a distance that the fork prongs 26 of the aiming gauge 25 can be pushed into the sleeves 38, 39. This is done in the direction of arrow 40.

On the pivotable bracket plate 3 two bearing blocks 41 and 42 are welded at a distance from each other for a shaft 43 carrying interlocking cams 8 at its extremities projecting from the bearing blocks 41 and 42, these cams are fixedly secured to the shaft for rotational movement therewith. The interlocking cams 8 are of eccentric form and partially extend through slots 44 in the bracket plate 3. In the position shown in FIG. 3, a portion of the cam extends through an opening, not shown, of the sleeves 38 and 39, in order to arrest the fork prongs 26 within the sleeves 38 and 39. If the shaft 43 is turned counterclockwise, the arresting mechanism is released.

In the following the actuation of shaft 43 will be described and with that of the interlocking cams 8.

The shaft 43 is extended through a crank arm 45 and is connected thereto in a way so as not to permit rotation therewith. A connecting rod is linked to the bifurcated crank arm 45, the connecting rod comprises two parts 46 and 47. Part 47 has a threaded portion, which can be screwed into a threaded bore of part 46. Part 47 is pivotally joined to the one extremity of crank arm 48 cooperating at its lower extremity with the crank shaft 50. Crank shaft 50 is rotatably received in the holes of bearing blocks 55 and 56. The eccentric plates 52 and 53 are connected rigidly to the crank shaft 50. The bearing blocks 55 and 56 are welded to the bracket plate 3. Annular portions 57 and 58 are secured to the ends of the crank shaft 50 for rotation therewith, the annular portions in turn are screwed onto a U-shaped bundle 9. It should be mentioned that spacer washers 60 and 61 are disposed between the bearing blocks 55 and 56 and the eccentric plates 52 and 53. It can be seen that connecting rod 46–47 is axially adjusted upon pivotal movement of the handle 9 through the crank shaft 50 and the crank arm 48 thus effecting rotation of shaft 43 and of the locking cams 8. In the position shown in FIG. 5 the eccentric plates 52 and 53 cooperate in a self-locking manner with resilient shoes 62 and 63, that are screwed on the upper side of the bracket plate 3 when the plate is viewed as in FIG. 5.

The parts 46 and 47 of the connecting rod can be moved relative to each other. For this it is necessary to release part 47 from the crank arm 48, so that it can be rotated with respect to part 46. In this way it is possible to vary the tension with which the cams 8 urge against the prongs 26 of the aiming gauge 25.

The base plate 12 extends beyond the bracket plate 3 at the opposite extremity thereof and retains at this end a locking mechanism 14, having a pawl 67 and an unlocking lever 68. With the bracket plate 3 a locking tongue 64 is connected, of which the part which is placed slightly beyond the edge of the bracket plate cooperates with pawl 67. Upon pivoting of bracket plate 3 towards the base plate 12 the locking tongue 64 trips automatically beneath pawl 67, so as to be able to be locked in the position illustrated in FIG. 5. The interlocking engagement can then be released by manual actuation of the unlocking lever 68.

In the position shown in FIG. 5 the eccentric plates 52 and 53 are lying in close contact and under tension against the resilient shoes 62 and 63 so that the screws 65 and 66 compensate for possible existing clearances between plates 12 and 3, because the screws extend through plate 3 and are forced onto the base plate 12 by the eccentric plates 52 and 53. The adjusting screws 65 and 66 in the shoes 62 and 63 secure an exact adjustment.

The aiming procedure starts with orienting the X-ray source 4 perpendicularly with respect to the axis of nail 6 and centering it on one of the holes 6-2 in the distal end of the nail 6. In this way the circular form of this hole appears on the monitor which image is overlapped with the image of the reception socket 7. This image must be checked after each operating step and if it is necessary be adjusted again. After having made the incision the aiming sleeve 32 inserted in socket 7 is moved adjacent the corticalis and fixed within its socket 7. Further working is now performed with the aid of the aiming sleeve.

We claim:

1. An aiming device for fasteners of an implanted bone nail, said device being suitable for use with a Roentgen ray source having an exit window emitting a radiation beam, said device comprising:
    a reception socket (7) for receiving a fastener aiming sleeve (32);
    support means (25) for said reception socket; and
    mounting means (3,12) for joining said support means with the housing (21) of the Roentgen ray source (4),
    said support means comprising means for positioning said reception socket spaced from the exit window (22) of the Roentgen ray source and approximately in the center of the radiation beam of the source.

2. The device according to claim 1 wherein said reception socket has a hole in the bottom thereof, said socket being adjustable with respect to said support means (25).

3. The device according to claim 2 wherein said support means includes a fork-like element (26, 28, 29) having a pair of prongs joined to a common portion, wherein said reception socket is mounted on said common portion, and wherein said mounting means (12, 3) has a pair of sleeves (38, 39) for receiving the prongs of the fork.

4. The device according to claim 3, characterized in that at least one locking element (8) is mounted on the mounting means for securing the fork-like element (26, 28, 29) in selected positions.

5. The device according to claim 4, characterized in that the mounting means comprises a base plate (12) connectable to the Roentgen ray source housing and a bracket plate (3) which is pivotally mounted on the base plate (12) and contains the sleeves (38 and 39).

6. The device according to claim 5, characterized in that, on the base plate, a manually operable locking mechanism (14) is mounted and the pivotable bracket plate (3) includes a locking portion (64) which can be brought into interlocking engagement with the locking mechanism (14).

7. The device according to claim 5, characterized in that the locking element is an eccentric locking cam (8) connected with a rotary shaft (43) journalled in said mounting means and placed in an opening area of each of said sleeves (38 and 39) and the rotary shaft (43) is connected to a bell crank linkage arranged on the bracket plate (3).

8. The device according to claim 7, characterized in that a pivotable arm (45) is connected to the rotary shaft (43) and to an actuating portion (46 and 47) which, in turn, is pivotally connected to a second pivotable arm (48), said second arm being rigidly connected to a second rotary shaft (50) journalled in said bracket plate (3) and on which shaft is fixed eccentric retaining plates (52, 53), said second shaft having a handle (9) for rotating same.

9. The device according to claim 8, characterized in that the eccentric plates (52, 53) are arranged in such a way that in the locking position they are in self-locking engagement with resilient shoes (62 and 63) on the pivotable bracket plate (3).

10. The device according to claim 9, characterized in that at least portions of bracket plate (3) and base plate (12) lie parallel when in the locking position and that adjusting screws (65, 66) for said resilient shoes are mounted such that they extend through bracket plate (3) when in the locking position and are forced onto the base plate (12), thereby to compensate for any clearance existing between the bracket plate (3) and base plate (12).

* * * * *